United States Patent [19]

Akiyama et al.

[11] 4,075,244
[45] Feb. 21, 1978

[54] PROCESS FOR PREPARING METHACRYLIC ACID

[75] Inventors: Shinichi Akiyama; Haruhisa Yamamoto, both of Takaoka, Japan

[73] Assignee: Nippon Zeon Co. Ltd., Tokyo, Japan

[21] Appl. No.: 735,550

[22] Filed: Oct. 26, 1976

Related U.S. Application Data

[63] Continuation of Ser. No. 523,684, Nov. 14, 1974, abandoned.

[30] Foreign Application Priority Data

Nov. 22, 1973 Japan .................................. 48-131325
Mar. 14, 1974 Japan .................................. 49-29405

[51] Int. Cl.² ............................................. C07C 51/32
[52] U.S. Cl. ............................... 260/530 N; 252/435; 252/437
[58] Field of Search .................... 260/530 N; 252/435, 252/437

[56] References Cited

U.S. PATENT DOCUMENTS

| 3,795,703 | 3/1974 | Niina et al. ........................ 260/530 N |
| 3,857,796 | 12/1974 | Takenaka et al. ................ 260/530 N |
| 3,865,873 | 2/1975 | Oda et al. ......................... 260/530 N |
| 3,875,220 | 4/1975 | White et al. ...................... 260/530 N |
| 3,925,464 | 12/1975 | Oda et al. ......................... 260/530 N |
| 3,976,688 | 8/1976 | Akiyama et al. ................. 260/530 N |

*Primary Examiner*—Vivian Garner
*Attorney, Agent, or Firm*—Sherman & Shalloway

[57] ABSTRACT

A process for the preparation of methacrylic acid which comprises reacting methacrolein with molecular oxygen in the vapor phase in the presence of an oxidation catalyst composition having the following empirical formula

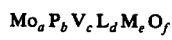

$$Mo_a P_b V_c L_d M_e O_f$$

wherein L is at least one element selected from the group consisting of Rb, Cs and K; M is at least one element selected from the group consisting of Sr, Zn, Cd, Nb, B, Pb, and W; and $a$, $b$, $c$, $d$, $e$ and $f$ each represent the number of atoms of each element; the atomic ratio of $a:b:c:d:e$ is 12:0.1–8:0–.1–8:0.1–8:0–6; and $f$ is the number of oxygen atoms determined by the valence requirement of the other elements present.

17 Claims, No Drawings

PROCESS FOR PREPARING METHACRYLIC ACID

This is a continuation of application Ser. No. 523,684, filed Nov. 14, 1974, now abandoned.

This invention relates to a process for preparing methacrylic acid by the vapor phase oxidation of methacrolein using a specific catalyst which can give the methacrylic acid in high selectivity and yield and has a long active lifetime.

Prior patents and literature relating to the vapor phase catalytic oxidation of unsaturated aldehydes are directed chiefly to the production of acrylic acid from acrolein, and very few relate to the production of methacrylic acid from methacrolein. Actually, many of the catalysts which give good results in the oxidation of acrolein exhibit low activity (low conversion) when applied to the oxidation of methacrolein. If the reaction is carried out at an elevated temperature in order to increase the conversion of methacrolein, side-reactions such as a complete oxidation reaction (the formation of CO and $CO_2$) occur to reduce the yield (per pass) and selectivity of methacrylic acid. On the other hand, the catalysts so far suggested for the oxidation of methacrolein are commercially unsuitable and not entirely satisfactory for one or combinations of the following reasons, such as low activity, short active life and low productivity (space time yield for methacrylic acid) because of the necessity to prolong the reaction time or to reduce the methacrolein concentration in the feed gas.

Under such circumstances, it has been considered very difficult to produce methacrylic acid commercially by the oxidation of methacrolein, in spite of the fact that the production of acrylic acid from acrolein has been carried out commercially. Accordingly, it has been concluded that the development of catalysts useful for the oxidation of methacrolein must be studied with different considerations than the catalysts used for the oxidation of acrolein.

Accordingly, it is an object of this invention to provide a new catalyst which can be used as an oxidation catalyst and which eliminates the defects of conventional oxidation catalysts for methacrolein, and which has excellent catalytic activity (namely, giving high yield, selectivity and productivity of methacrylic acid) and a long active lifetime.

This object of the invention can be achieved by using an oxidation catalyst composition comprising a catalytic oxide of molybdenum, phosphorus, vanadium and at least one element selected from the group consisting of rubidium, cesium and potassium, as essential catalytic ingredients, the catalyst composition having the following empirical formula

wherein L is at least one element selected from the group consisting of Rb, Cs and K; M is at least one element selected from the group consisting of Sr, Zn, Cd, Nb, B, Pb, and W; and $a$, $b$, $c$, $d$, $e$ and $f$ each represent the number of atoms of each element; the preferred atomic ratio of $a:b:c:d:e$ is in the range of about 12:0.1–8:0.1–8:0.1–8:0–6; and $f$ is the number of oxygen atoms determined by the valence requirements of the other elements present; a more preferred atomic ratio of $a:b:c:d$ is in the range of about 12:0.3–5:0.3–5:0.3–5:0–3.

The catalyst according to the present invention can be used as an oxidation catalyst to produce methacrylic acid in higher yields and selectivities than conventional catalysts used in the stable oxidation reaction of unsaturated aldehydes under feasible reaction conditions. Furthermore, the problem of the active lifetime of the catalyst has now been solved by the new catalyst used in this invention. Since the catalytic life can be maintained at a high level for prolonged periods of time, the reaction can be performed continuously over an extended period of time.

The catalyst of this invention can contain ingredient M as a promotor. The inclusion of this ingredient gives rise to a further increase in catalytic activity. The preferred atomic ratio of $a:b:c:d:e$ of a catalyst containing ingredient M is 12:0.3–5:0.3–5:0.3–5:0.05–3.

The catalyst may be made, for example, by the oxide mixing method, the evaporative drying method or the coprecipitation method, all of which are well known in the art. The starting constituent elements of the catalyst do not always have to be in the form of an oxide but may be in the form of a metal, metal salt, acid or base so long as they can be converted to the corresponding metal oxides by calcination. Typical examples include salts such as ammonium salts, nitrate or halides; free acids such as molybdic acid or phosphoric acid; heteropolyacids containing molybdenum, such as phosphomolybdic acid, and heteropolyacid salts such as the ammonium salt of phosphomolybdic acid. Prior to use, the catalyst composition is preferably calcined for several hours up to 15 or 16 hours at about 250°–700° C., preferably about 350°–600° C. in air, a reducing atmosphere or feed gas.

The catalyst can be prepared, for example, by admixing an aqueous molybdate solution such as ammonium molybdate, with an aqueous solution containing a vanadium compound, adding an aqueous solution containing phosphoric acid and an aqueous solution containing a water-soluble compound of L element, followed, if desired, by further adding an aqueous solution containing a water-soluble compound of M element, then evaporatively drying the entire mixture with stirring, calcining the solid obtained, pulverizing the calcined product, and then, if necessary, molding it into a suitable shape. Other examples of the catalyst preparation are described for example, in the working examples to be given later. Preferably, the catalyst is prepared by mixing the starting compounds so that the constituent elements will form complex compounds such as heteropolyacids, their acid salts or ammonium salts, calcining the obtained complex compounds to produce the corresponding oxides in situ, pulverizing the calcined product and then, if necessary, molding it into pellets. Those skilled in the art can select the desired method of preparing the catalyst. It is not yet clear however, in what state the individual elements of the catalyst composition, including oxygen, are during the reaction when the catalyst is exhibiting its catalytic action.

While the catalyst can be used in the molded or powdered form, it is also possible to use it after dilution with an inert diluent. If desired, the catalyst can be deposited on a suitable inert carrier material. Examples of suitable carriers include alumina, silicon carbide, graphite, inert titania, zirconium oxide thorium chloride, pumice, silica gel, or celite. The amount of diluent or carrier is not critical since it has no substantial effect on the activity of the catalyst.

The source of molecular oxygen can be pure oxygen or air. Furthermore, it is possible to introduce into the reaction zone an inert diluent gas such as steam, nitrogen, argon, carbon dioxide, helium or a saturated hydrocarbon, for example, methane, ethane or propane.

The concentration of methacrolein in the feed gas to be introduced into the reactor is preferably from about 1 to about 25% by volume. On the other hand, the molar ratio of methacrolein to molecular oxygen is conveniently about 1:(0.1–25.0), preferably about 1:(0.1–20.0). The reaction temperature is usually in the range of about 300° to 500° C., preferably about 330° to about 450° C. and the reaction pressure can be from a reduced pressure of less than atmospheric pressure to a superatmospheric pressure up to about 15 atoms. Preferably, the reaction pressure is about 0.5 to about 10 atmospheres. The contact time (on the basis of 0° C. and 1 atm.) is from about 0.1 to about 20 seconds, preferably about 0.1 to about 15 seconds. The type of reactor with which the catalysts of the present invention may be used may be any of those which are conventional, such as the fluidized, moving or fixed bed type. The reaction product can be recovered by known techniques; for example, condensation and liquiefaction by means of a condenser or the extraction by water or a suitable solvent.

The invention is illustrated by the following Examples in which the catalysts are used in the conversion of methacrolein. The conversion of methacrolein, the yield of methacrylic acid and the selectivity therefor are defined below. The analysis was carried out by gas chromatography in all cases.

Conversion (%) = 
$$\frac{\text{methacrolein fed (mol)} - \text{unreacted methacrolein (mol)}}{\text{methacrolein fed (mol)}} \times 100$$

Yield (%) = $\frac{\text{methacrylic acid formed (mol)}}{\text{methacrolein fed (mol)}} \times 100$ Selectivity (%) = $\frac{\text{Yield}}{\text{conversion}} \times 100$ The abbreviations used in the tables appearing in the Examples have the following meanings.
Cat. = catalyst
RT = reaction temperature
MAL = methacrolein
MAA = methacrylic acid
conv. = conversion
sel. = selectivity.

Furthermore, in the following Examples, the indication of the composition of the catalyst does not specifically refer to the presence of oxygen.

EXAMPLE 1

Ammonium molybdate (212 g) was dissolved in 300 ml. of water with heating. Ammonium metavanadate (23.4g) was dissolved in 200 ml. of a warm aqueous solution of 35.1g of oxalic acid, and the solution was added to the aqueous ammonium molybdate solution prepared above, followed by stirring the mixture. Furthermore, an aqueous solution of 23 g of 85 wt% phosphoric acid in 50 ml. of water and an aqueous solution obtained by dissolving 39.0g of cesium nitrate ($CsNO_3$) in 200 ml. of water with heating were added to the mixture, and the entire mixture was evaporated to dryness with stirring. The solid obtained was calcined at 430° C. for 16 hours in a muffle furnace, pulverized, and screened to a screen size of 4 to 8 mesh (Tyler No. 4–No. 8, 4.00 mm–2.38 mm).

The atomic ratio of Mo:P:V:Cs of the resulting catalyst composition (Cat. No. 1) was 12:2:1:2.

Catalysts indicated in Table 1 were prepared in the same way except using 20.2 g of potassium nitrate ($KNO_3$), and 29.5 g of rubidium nitrate ($RbNO_3$) respectively instead of the cesium nitrate ($CsNO_3$). Comparison catalysts indicated in Table 1 were also prepared in the same way with the proviso that those not containing V component were calcined at 450° C.

A stainless steel reaction tube 2.5 cm in inside diameter and 60 cm in length was packed with 100 ml. of the catalyst, and heated by a molten metal bath. A feed gas having a methacrolein:$O_2$:$N_2$:$H_2O$ molar ratio of 1:1.5:17.5:10 was passed through the reaction tube while the contact time was adjusted to 1.8 seconds (on the basis of 0° C., and 1 atm.). The results obtained are shown in Table 1.

The reaction temperatures shown in Table 1 are the maximum temperatures of the catalyst layer at which the best results were obtained.

The results shown in Table 1 demonstrate that, in spite of the short contact time, the catalysts of the present invention give methacrylic acid in high selectivity and yield. This also shows that the catalysts of this invention give excellent space time yield for methacrylic acid.

Table 1

| Run No. | Cat. No. | Catalyst composition (atomic ratio) | RT (° C) | MAL conv. (%) | MAA Yield (Sel.) (%) |
|---|---|---|---|---|---|
| | | This invention | | | |
| I-1 | 1 | $Mo_{12}P_2V_1Cs_2$ | 400 | 80.0 | 63.8 (79.8) |
| -2 | 2 | $Mo_{12}P_2V_1K_2$ | 406 | 70.3 | 50.2 (71.4) |
| -3 | 3 | $Mo_{12}P_2V_1Rb_2$ | 405 | 76.9 | 56.1 (73.0) |
| | | Comparison | | | |
| I-5 | C-1 | $Mo_{12}P_2V_1$ | 421 | 43.8 | 26.3 (60.0) |
| -6 | C-2 | $Mo_{12}P_2Cs_2$ | 409 | 47.1 | 28.3 (60.1) |
| -7 | C-3 | $Mo_{12}P_2K_2$ | 419 | 42.1 | 19.1 (45.4) |
| -8 | C-4 | $Mo_{12}P_2Rb_2$ | 416 | 44.6 | 25.3 (56.7) |
| -9 | C-5 | $Mo_{12}P_2Tl_2$ | 421 | 45.0 | 28.4 (63.0) |
| -10 | C-6 | $Mo_{12}Tl_2V_1$ | 395 | 44.1 | 8.3 (18.8) |
| -11 | C-7 | $Mo_{12}Cs_2V_1$ | 390 | 50.5 | 10.1 (20.0) |
| -12 | C-8 | $Mo_{12}K_2V_1$ | 398 | 39.0 | 6.4 (16.4) |
| -13 | C-9 | $Mo_{12}Rb_2V_1$ | 395 | 39.3 | 6.8 (17.3) |

EXAMPLE 2

The procedure of Example 1 was repeated to prepare catalysts shown in Table 2, and the same reaction as in Example 1 was performed. The results obtained are shown in Table 2.

Table 2

| Run No. | Cat. No. | Catalyst composition (atomic ratio) | RT (° C) | MAL conv. (%) | MAA Yield (Sel.) (%) |
|---|---|---|---|---|---|
| II-1 | 5 | $Mo_{12}P_2V_{0.5}Cs_2$ | 401 | 76.9 | 59.2 (77.0) |
| -2 | 6 | $Mo_{12}P_2V_2Cs_2$ | 425 | 82.0 | 51.1 (62.3) |
| -3 | 7 | $Mo_{12}P_2V_1Cs_1$ | 395 | 82.4 | 56.7 (68.8) |
| -4 | 8 | $Mo_{12}P_1V_1Cs_{0.5}$ | 370 | 80.0 | 47.3 (59.1) |
| -5 | 9 | $Mo_{12}P_{0.5}V_{1.5}Cs_1$ | 379 | 78.4 | 47.8 (61.0) |
| -6 | 10 | $Mo_{12}P_3V_1Cs_2$ | 410 | 74.3 | 55.0 (74.0) |
| -7 | 11 | $Mo_{12}P_2V_{0.5}K_1$ | 405 | 70.3 | 49.9 (71.0) |
| -8 | 12 | $Mo_{12}P_1V_1K_{0.5}$ | 371 | 71.1 | 45.3 (63.7) |
| -9 | 13 | $Mo_{12}P_2V_{0.5}Rb_1$ | 403 | 70.8 | 51.3 (72.5) |
| -10 | 14 | $Mo_{12}P_1V_1Rb_{0.5}$ | 370 | 74.8 | 46.0 (61.5) |
| -11 | 15 | $Mo_{12}P_2Cs_1Rb_1V_1$ | 405 | 79.4 | 58.9 (74.2) |

EXAMPLE 3

1. Ammonium molybdate (212 g) was dissolved in 300 ml. of water with heating. Ammonium metavanadate (23.4g) was dissolved in 200 ml. of a warm aqueous solution of 35.1 g of oxalic acid, and the solution was added to the aqueous ammonium molybdate solution prepared above, followed by stirring the mixture. Furthermore, an aqueous solution of 23 g of 85 wt.% phosphoric acid in 50 ml. of water, an aqueous solution obtained by dissolving 39.0g of cesium nitrate ($CsNO_3$) in 200 ml. of water with heating, and an aqueous solution of 10.55 g of strontium nitrate $Sr(NO_3)_2$ in 200 ml. of water were added to the mixture, and the entire mixture was evaporated to dryness with stirring. The solid obtained was calcined at 430° C. for 16 hours in a muffle furnace, pulverized, and screened to a screen size of 4 to 8 mesh (Tyler No. 4–No. 8, 4.00 mm–2.38 mm).

The atomic ratio of Mo:P:V:Cs:Sr of the resulting catalyst composition (Cat. No. 20) was 12:2:1:2:0.5.

Similarly, Cat. No. 21 to Cat. No. 29 were prepared using 7.43 g of $Zn(NO_3)_2 \cdot 6H_2O$, 7.7g of $Cd(NO_3)_2 \cdot 4H_2O$, 13.45 g of $Nb(HC_2O_4)_5$, 3.1 g of $H_3BO_3$, 16.55 g of $Pb(NO_3)_2$ and 26.1 g of $(NH_4)_{10}W_{12}O_{41} \cdot 5H_2O$ instead of $Sr(NO_3)_2$.

2. Cat. No. 30 to Cat. No. 38 were prepared in the same way as (1) above using 20.2 g of $KNO_3$ and 29.5 g of $RbNO_3$ instead of $Cs(NO_3)$.

3. For comparison, Cat. No. (C-10) to Cat. No. (C-17) were prepared in the same way as in (1) and (2) above, except that those catalysts not containing a vanadium ingredient were calcined at 450° C.

Methacrolein was oxidized under the same conditions as in Example 1 using each of these catalysts. The results are shown in Table 3.

Table 3

| Run No. | Cat. No. | Catalyst composition (atomic ratio) | RI (°C) | MAL conv. (%) | MAA Yield (Sel.) (%) |
|---|---|---|---|---|---|
| | | This invention | | | |
| III-1 | 20 | $Mo_{12}P_2V_1Cs_2Sr_{0.5}$ | 418 | 85.7 | 69.5 (81.1) |
| -2 | 21 | $Mo_{12}P_2V_{0.5}Cs_2Sr_{0.5}$ | 421 | 81.8 | 65.8 (80.4) |
| -3 | 22 | $Mo_{12}P_2V_1Cs_2Sr_{0.25}$ | 415 | 84.7 | 68.6 (81.0) |
| -4 | 23 | $Mo_{12}P_2V_1Cs_2Zn_{0.25}$ | 413 | 80.5 | 67.4 (83.7) |
| -5 | 24 | $Mo_{12}P_2V_1Cs_2Ca_{0.25}$ | 416 | 85.7 | 68.9 (80.4) |

Table 3-continued

| Run No. | Cat. No. | Catalyst composition (atomic ratio) | RI (°C) | MAL conv. (%) | MAA Yield (Sel.) (%) |
|---|---|---|---|---|---|
| -6 | 25 | $Mo_{12}P_2V_1Cs_2Nb_{0.5}$ | 403 | 83.7 | 68.1 (81.4) |
| -7 | 26 | $Mo_{12}P_2V_1Cs_2Nb_{0.25}$ | 400 | 82.5 | 70.1 (85.0) |
| -8 | 27 | $Mo_{12}P_2V_1Cs_2B_{0.5}$ | 421 | 82.0 | 69.7 (85.0) |
| -9 | 28 | $Mo_{12}P_2V_1Cs_2Pb_{0.5}$ | 401 | 83.0 | 68.3 (82.3) |
| -10 | 29 | $Mo_{12}P_2V_1Cs_2W_1$ | 404 | 82.8 | 69.8 (84.3) |
| -11 | 30 | $Mo_{12}P_2V_1H_2Sr_{0.5}$ | 420 | 77.4 | 57.4 (74.2) |
| -12 | 31 | $Mo_{12}P_2V_1H_2Zn_{0.25}$ | 412 | 73.6 | 54.8 (74.5) |
| -13 | 32 | $Mo_{12}P_2V_1K_2S_{0.5}$ | 426 | 76.3 | 58.0 (76.0) |
| -14 | 33 | $Mo_{12}P_2V_1Rb_2Sr_{0.5}$ | 417 | 81.6 | 61.9 (75.9) |
| -15 | 34 | $Mo_{12}P_2V_{0.5}Rb_2S_{0.5}$ | 420 | 77.0 | 57.1 (74.2) |
| -16 | 35 | $Mo_{12}P_2V_1Rb_2Nb_{0.25}$ | 400 | 79.8 | 62.9 (78.8) |
| -17 | 36 | $Mo_{12}P_2V_1Rb_2Pb_{0.5}$ | 408 | 79.6 | 61.1 (76.8) |
| -18 | 37 | $Mo_{12}P_2V_1Cs_2W_{0.5}Nb_{0.25}$ | 402 | 81.6 | 69.4 (85.0) |
| -19 | 38 | $Mo_{12}P_2V_1Cs_2Sr_{0.25}B_{0.25}$ | 416 | 81.1 | 68.3 (84.5) |
| | | Control | | | |
| -20 | C-10 | $Mo_{12}P_2V_1Sr_{0.5}$ | 410 | 58.4 | 38.1 (63.2) |
| -21 | C-11 | $Mo_{12}P_2V_1Sr_{0.25}$ | 420 | 42.0 | 24.3 (57.9) |
| -22 | C-12 | $Mo_{12}P_2V_1Nb_{0.25}$ | 424 | 45.8 | 27.7 (60.5) |
| -23 | C-13 | $Mo_{12}P_2V_1W_1$ | 420 | 43.7 | 25.8 (59.1) |
| -24 | C-14 | $Mo_{12}P_2Cs_2B_{0.5}$ | 416 | 63.1 | 44.3 (70.2) |
| -25 | C-15 | $Mo_{12}P_2Ti_2Cl_{0.25}$ | 414 | 38.5 | 38.0 (65.0) |
| -26 | C-16 | $Mo_{12}P_2K_2Zn_{0.25}$ | 412 | 44.9 | 28.6 (63.7) |
| -27 | C-17 | $Mo_{12}P_2Rb_2Pb_{0.5}$ | 405 | 33.4 | 30.6 (57.3) |

EXAMPLE 4

Methacrolein was ozidized continuously for prolonged periods of time under the same conditions in Example 1 using each of th catalysts shown in Table 4 which were obtained in Examples 1, 2 and 3. The performance of each catalyst used after a lapse of 30 days from the initiation of the reaction is shown in Table 5. The temperature of the molten metal bath was kept almost constant during the reaction. In the table, "O" under headline "time that elapsed" means the initial stage of the reaction. It can be seen from Table 4 that the catalysts prepared according to the present invention do not lose their activity even after a lapse of a long period of time, and prove to be excellent catalysts having a very long active lifetime. On the other hand, the activity of the comparison catalysts decreases abruptly within a short period of time, and therefore, they have a short active lifetime.

Table 4

| Run No. | Cat. No. | Catalyst composition (atomic ratio) | Time that elapsed (days) | RT (°C) | MAL conv. (%) | MAA Yield (Sel) (%) |
|---|---|---|---|---|---|---|
| | | This invention | | | | |
| IV-1 | 1 | $Mo_{12} P_2 V_1 Cs_2$ | 0* | 400 | 80.0 | 63.8 (79.8) |
| | | | 30 | 400 | 78.8 | 63.5 (80.6) |
| -2 | 2 | $Mo_{12} P_2 V_1 K_2$ | 0 | 406 | 70.3 | 50.2 (71.4) |
| | | | 30 | 409 | 71.1 | 49.0 (68.9) |
| -3 | 3 | $Mo_{12} P_2 V_1 Rb_2$ | 0 | 405 | 76.9 | 56.1 (73.0) |
| | | | 30 | 407 | 76.0 | 55.0 (72.4) |
| -4 | 20 | $Mo_{12} P_2 V_1 Cs_2 Sr_{0.5}$ | 0* | 418 | 85.7 | 69.5 (81.1) |
| | | | 30 | 415 | 84.7 | 69.0 (81.5) |
| -5 | 28 | $Mo_{12} P_2 V_1 Cs_2 Pb_{0.5}$ | 0 | 401 | 83.0 | 68.3 (82.3) |
| | | | 30 | 400 | 82.6 | 68.5 (82.9) |
| -6 | 32 | $Mo_{12} P_2 V_1 K_2 B_{0.5}$ | 0 | 426 | 76.3 | 58.0 (76.0) |
| | | | 30 | 424 | 75.4 | 57.5 (76.3) |
| -7 | 35 | $Mo_{12} P_2 V_1 Rb_2 Nb_{0.25}$ | 0 | 400 | 79.8 | 62.9 (78.8) |
| | | | 30 | 402 | 80.6 | 62.9 (78.0) |
| | | Comparison | | | | |
| -8 | C-1 | $Mo_{12} P_2 V_1$ | 0 | 421 | 43.8 | 26.3 (60.0) |
| | | | 10 | 428 | 49.6 | 20.0 (40.3) |
| -9 | C-2 | $Mo_{12} P_2 Cs_2$ | 0 | 409 | 47.1 | 28.3 (60.1) |
| | | | 30 | 386 | 38.2 | 19.5 (51.0) |
| -10 | C-3 | $Mo_{12} P_2 K_2$ | 0 | 419 | 42.1 | 19.1 (45.4) |
| | | | 30 | 390 | 31.4 | 10.0 (31.8) |
| -11 | C-4 | $Mo_{12} P_2 Rb_2$ | 0 | 416 | 44.6 | 25.3 (56.7) |
| | | | 30 | 410 | 32.6 | 15.9 (48.8) |
| -12 | C-5 | $Mo_{12} P_2 Tl_2$ | 0 | 421 | 45.0 | 28.4 (63.0) |
| | | | 30 | 415 | 36.5 | 18.7 (51.2) |
| -13 | C-6 | $Mo_{12} Tl_2 V_1$ | 0 | 395 | 44.1 | 8.3 (18.8) |
| | | | 6 | 401 | 50.4 | 6.1 (12.1) |
| -14 | C-7 | $Mo_{12} V_1 Cs_2$ | 0 | 390 | 50.5 | 10.1 (20.0) |

Table 4-continued

| Run No. | Cat. No. | Catalyst composition (atomic ratio) | Time that elapsed (days) | RT (° C) | MAL conv. (%) | MAA Yield (Sel) (%) |
|---|---|---|---|---|---|---|
| | | | 6 | 399 | 54.7 | 7.9 (14.4) |

What is claimed is:

1. A process for the preparation of methacrylic acid which comprises reacting methacrolein with molecular oxygen in the vapor phase in the presence of an oxidation catalyst composition consisting essentially of a catalytic oxide of molybdenum (Mo), phosphorous (P), vanadium (V), at least one of rubidium (Rb), cesium (Cs), or potassium (K), and optionally at least one of strontium (Sr), zinc (Zn), cadmium (Cd), niobium (Nb), boron (B), lead (Pb) or tungsten (W), said catalyst composition having the following empirical formula:

$$Mo_a P_b V_c L_d M_e O_f$$

wherein L is at least one element selected from the group consisting of Rb, Cs and K; M is at least one element selected from the group consisting of Sr, Zn, Cd, Nb, B, Pb, and W; and $a$, $b$, $c$, $d$, $e$, and $f$ each represent the number of atoms of each element; the atomic ratio of $a:b:c:d:e$ is 12:0.1–8:0.1–8:0.1–8:0.6; and $f$ is the number of oxygen atoms determined by the valence requirement of the other elements present.

2. The process of claim 1, wherein the reaction temperature is 300° to 500° C.

3. The process of claim 1, wherein the source of the molecular oxygen is air.

4. The process of claim 1, wherein an inert diluent gas is introduced into the reaction zone.

5. The process of claim 1, wherein the catalyst is diluted with an inert diluent or supported on an inert carrier.

6. The process of claim 1, wherein the atomic ratio of $a:b:c:d:e$ is 12:0.3–5:0.3–5:0.3–5:0–3.

7. The process of claim 1, wherein L is Rb.

8. The process of claim 1, wherein L is Cs.

9. The process of claim 1, wherein L is K.

10. The process of claim 1, wherein the atomic ratio of $a:b:c:d:e$ is 12:0.3–5:0.3–5:0.3–5:0.05–3.

11. The process of claim 10 wherein M is Sr.
12. The process of claim 10 wherein M is Zn.
13. The process of claim 10 wherein M is Cd.
14. The process of claim 10 wherein M is Pb.
15. The process of claim 10 wherein M is Nb.
16. The process of claim 10 wherein M is B.
17. The process of claim 10 wherein M is W.

UNITED STATES PATENT OFFICE
CERTIFICATE OF CORRECTION

Patent No. 4,075,244            Dated February 21, 1978

Inventor(s) Akiyama, et al.

It is certified that error appears in the above-identified patent and that said Letters Patent are hereby corrected as shown below:

Claim 1, line 17, delete "12:0.1-8:0.1-8:0.1-8:0.6",
    insert --12:0.1-8:0.1-8:0.1-8:0-6--

*Signed and Sealed this*

*Twenty-seventh* Day of *June 1978*

[SEAL]

*Attest:*

RUTH C. MASON
*Attesting Officer*

DONALD W. BANNER
*Commissioner of Patents and Trademarks*